US011779708B2

(12) United States Patent
Helmer et al.

(10) Patent No.: US 11,779,708 B2
(45) Date of Patent: Oct. 10, 2023

(54) DRUG DELIVERY DEVICE

(71) Applicant: SANOFI, Paris (FR)

(72) Inventors: Michael Helmer, Frankfurt am Main (DE); Christian Rehbein, Nieder-Olm (DE)

(73) Assignee: Sanofi, Paris (FR)

( * ) Notice: Subject to any disclaimer, the term of this patent is extended or adjusted under 35 U.S.C. 154(b) by 612 days.

(21) Appl. No.: 16/956,397

(22) PCT Filed: Dec. 18, 2018

(86) PCT No.: PCT/EP2018/085396
§ 371 (c)(1),
(2) Date: Jun. 19, 2020

(87) PCT Pub. No.: WO2019/121617
PCT Pub. Date: Jun. 27, 2019

(65) Prior Publication Data
US 2020/0360615 A1    Nov. 19, 2020

(30) Foreign Application Priority Data

Dec. 22, 2017    (EP) .................................... 17306895

(51) Int. Cl.
*A61M 5/20*    (2006.01)
*A61M 5/315*    (2006.01)
(Continued)

(52) U.S. Cl.
CPC ...... *A61M 5/31551* (2013.01); *A61M 5/2033* (2013.01); *A61M 5/3157* (2013.01);
(Continued)

(58) Field of Classification Search
CPC ............ A61M 5/31551; A61M 5/2033; A61M 5/3157; A61M 5/20; A61M 2005/3126;
(Continued)

(56) References Cited

U.S. PATENT DOCUMENTS 6,110,148 A    8/2000    Brown et al.
9,395,716 B2    7/2016    Bammer et al.
(Continued)

FOREIGN PATENT DOCUMENTS

CN    101268336    9/2008
CN    102413759    4/2012
(Continued)

OTHER PUBLICATIONS

PCT International Preliminary Report on Patentability in International Appln. No. PCT/EP2018/085396, dated Jun. 23, 2020, 8 pages.
(Continued)

*Primary Examiner* — Nathan R Price
*Assistant Examiner* — Tania Ismail
(74) *Attorney, Agent, or Firm* — Fish & Richardson P.C.

(57) ABSTRACT

A drug delivery device including: a body and a movable component arranged inside the body, a dosage selection and injection mechanism setting the position of the movable component inside the body depending on a selected dosage, a non-contact sensor configured to output signals indicative of the position of the movable component inside the body, and a processor. The processor is configured to receive the signals output from the non-contact sensor and to determine based on the signals whether the movable component is either in an initial position inside the body corresponding to no selected dosage or in a selected dosage position. Upon determining that the movable component has changed its position back from the selected dosage position to the initial position, the processor is configured to cause an indication to be output which informs a user regarding a dwell time of the drug delivery device.

20 Claims, 4 Drawing Sheets

(51) Int. Cl.
*G16H 20/17* (2018.01)
*G16H 40/63* (2018.01)
*G01B 7/02* (2006.01)
*A61M 5/31* (2006.01)

(52) U.S. Cl.
CPC ............ *G01B 7/023* (2013.01); *G16H 20/17* (2018.01); *G16H 40/63* (2018.01); *A61M 5/20* (2013.01); *A61M 2005/3126* (2013.01); *A61M 2205/3317* (2013.01); *A61M 2205/3584* (2013.01); *A61M 2205/52* (2013.01)

(58) Field of Classification Search
CPC ........ A61M 2205/337; A61M 2205/52; A61M 2205/3317; G16H 20/17
See application file for complete search history.

(56) References Cited

U.S. PATENT DOCUMENTS

2017/0056604 A1  3/2017  Cowan et al.
2018/0353699 A1* 12/2018  Helmer .................. A61M 5/20

FOREIGN PATENT DOCUMENTS

| | | |
|---|---|---|
| CN | 102458514 | 5/2012 |
| CN | 104203315 | 12/2014 |
| CN | 105431185 | 3/2016 |
| CN | 105792866 | 7/2016 |
| JP | 2015-532136 | 11/2015 |
| JP | 2016-523126 | 8/2016 |
| WO | WO 2007/039148 | 4/2007 |
| WO | WO 2010/098927 | 9/2010 |
| WO | WO 2010/142598 | 12/2010 |
| WO | WO 2012/046199 | 4/2012 |
| WO | WO 2013/050535 | 4/2013 |
| WO | WO 2013/120778 | 8/2013 |
| WO | WO 2014/116987 | 7/2014 |
| WO | WO 2014/195270 | 12/2014 |
| WO | WO 2015/084428 | 6/2015 |
| WO | WO 2017/050781 | 3/2017 |

OTHER PUBLICATIONS

PCT International Search Report and Written Opinion in International Appln. No. PCT/EP2018/085396, dated Feb. 21, 2019, 10 pages.

* cited by examiner

DRUG DELIVERY DEVICE

CROSS REFERENCE TO RELATED APPLICATIONS

The present application is the national stage entry of International Patent Application No. PCT/EP2018/085396, filed on Dec. 18, 2018, and claims priority to Application No. EP 17306895.8, filed on Dec. 22, 2017, the disclosures of which are incorporated herein by reference.

TECHNICAL FIELD

The present disclosure relates to a drug delivery device configured to inform a user of a dwell time, for example about the passed dwell time, after a medicament injection.

BACKGROUND

A variety of diseases exists that require regular treatment by injection of a medicament. Such injection can be performed by using injection devices, which are applied either by medical personnel or by patients themselves.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages for the user from this approach. If the user stops pressing the button/plunger, then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus, it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, allergies, hormone therapies, anticoagulants etc. Auto-injector devices can be used to deliver a single dose of a particular life-saving drug. For example, they are often prescribed to people who are at risk for anaphylaxis. They are also often used in the military to protect personnel from chemical warfare agents. Alternatively, auto-injectors are used to administer medicaments according to a prescribed therapeutic schedule for people suffering from Multiple Sclerosis, Rheumatroid Arthritis, Anemia, e.g.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, handshaking and the likelihood of delivering an incomplete dose are reduced. Triggering may be performed by numerous means, for example a trigger button or the action of the needle reaching its injection depth. In some devices, the energy to deliver the fluid is provided by a spring.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, whereas the syringe is disposed after having been spent and unloaded from the auto-injector. The syringe may be packaged with additional parts to provide additional functionality.

In a typical scenario, a disease can be treated by patients themselves by injection of medicament doses using an auto-injector, for example on a daily, weekly, bi-weekly, or monthly basis.

The correct administration of drugs and its termination is important for the safety and efficacy of the drug (pharmacovigilance). Failures in administration through the user can be minimized by monitoring of the injection device and the application time.

Typical patient failures are:
1. The user may forget the correct day of maturity for their next injection. This is particularly the case for medication intervals longer than a day, e.g. twice a week, every, second day, bi-weekly, or therapy specific intervals such as $1^{st}$ week twice, $2^{nd}$ week every $2^{nd}$ day, as of third week 2, 2, 3—interval, e.g.
2. The user may let too much time pass between removing the auto injector cap and performing the injection, resulting in needle clogging and/or device stalling.
3. The user does not carry out the holding time (also know as "dwell time") after the end of injection.

SUMMARY

This specification describes a drug delivery device, for example a one shot auto-injector, which may aid the patient in performing the injection correctly.

A first aspect provides a drug delivery device including a body and a movable component arranged inside the body, a dosage selection and injection mechanism setting the position of the movable component inside the body depending on a selected dosage, a non-contact sensor configured to output signals indicative of the position of the movable component inside the body, and a processor configured to receive the signals output from the non-contact sensor and to determine based on the signals whether the movable component is either in an initial position inside the body corresponding to no selected dosage or in a selected dosage position, wherein upon determining that the movable component has changed its position back from the selected dosage position to the initial position, the processor is configured to cause an indication to be output which informs a user regarding a dwell time of the drug delivery device.

This allows the drug delivery device to notify a user regarding the dwell time after the end of an injection and helps to improve the usage of the drug delivery device by the user. Using a non-contact sensor allows to monitor the drug delivery device without any increase in friction on the mechanical components of the drug delivery device. The moveable component within the drug delivery device and the dosage selection and injection mechanism are already present in the design of the drug delivery device and therefore no significant modifications to the way in which this drug delivery device operates are required to implement the device disclosed herein. Thus, the increases in the complexity of manufacture of the drug delivery device are minor.

The drug delivery device may further comprise a display unit. Causing an indication to be output may comprise causing one or more graphical elements to be displayed on the display unit, the graphical elements communicating a progress of the dwell time. Thus, a user can easily see the progress of the injection and how long to hold the device after the end of the injection.

The drug delivery device may further comprise a transmission unit. Causing an indication to be output may comprise causing one or more signals to be transmitted by the transmission unit, the signals communicating a progress of the dwell time. The transmitted signal(s) may for example be received by an external electronic device of the user, such as a computer or a smart phone, and processed by the device, for to notify a user of correct usage of the drug delivery device such as displaying assisting information, for example hints.

The transmission unit may be a wireless unit for transmitting data to one or more external devices. The transmitted data particularly comprises dwell time data and an identifier of the drug delivery device. For example, dwell time data could be transmitted to the user's computer or smart phone wirelessly, for example over a Bluetooth® connection. The user can for example install a program on its computer or smart phone for assisting and monitoring usage of the drug delivery device, and the program can process the data received from the transmission unit of the drug delivery device.

The non-contact sensor may be a capacitive sensor. A capacitive sensor may be implemented at relatively less technical expenses, particularly when using some of the components of the drug delivery device as sensor part. For example, the body, the movable component and the dosage selection and injection mechanism may form at least a part of a dielectric layer of the capacitive sensor. The position of the movable part inside the body may then influence the measured capacitance due to the changing air volume inside the body, i.e. when the movable part is moved far out of the body, the air volume inside the bode is higher than in case the movable part is moved inside the body. The changing air volume may cause a measurable capacitance change.

In order to obtain detectable capacitance changes of the capacitance sensor by the movable component, the body, the movable component and parts of the dosage selection and injection mechanism may be made of one or more materials selected to obtain a dielectric constant of the capacitive sensor sufficient to detect whether the movable component is either in an initial position inside the body corresponding to no selected dosage or in a selected dosage position, wherein the one or more selected materials may comprise plastics and particularly metal. In other words, the materials used for the body, the movable component and parts of the dosage selection and injection mechanism may be selected such that their dielectric constant creates a detectable capacitance, and that a movement of the movable component may alter the dielectric constant in a detectable range.

Particularly, at least one movable part of the dosage selection and injection mechanism may be made of metal, and the at least one metal part may influence the dielectric property of the capacitive sensor. For example, the at least one metal part of the dosage selection mechanism may be a drive spring of an injection mechanism of the drug delivery device.

The capacitive sensor may comprise opposing sets of at least two electrically conductive parts with a first part being a layer arranged on at least a part of the outside of the body. One or more of the at least two electrically conductive parts may be integrated into or arranged under a label of the drug delivery device. For example, a first part may be a metal layer deposited on a part of body. A second part of the at least two electrically conductive parts may be a layer being arranged on at least a part of the outside of the body and opposite to the first part. For example, the second part may be as the first part a metal lay deposited on the opposite side of the body, on which the first part is layered, such that the body, the movable component and most parts of the dosage selection and injection mechanism are arranged between the two metal layers and a capacitance may be obtained, which can be measured.

A second part of the at least two electrically conductive parts may be also arranged inside the body and opposite to the first part with the body, the movable component and the dosage selection and injection mechanism at least partly arranged between the first and the second part. For example, the second part may be a part of the dosage selection and injection mechanism, such as a metallic inner part, for example a spring.

The processor may be configured to measure the capacitance of the capacitive sensor when no dosage is selected and the movable component is in the initial position inside the body, to store the measured capacitance as reference value, to detect a capacitance change when a dosage is selected, to detect a further capacitance change due to an injection and to determine the end of the injection when the measured capacitance correlates with the reference value.

The dosage selection and injection mechanism may comprise a display for the selected dosage, wherein the display may be coupled to a rotatable component for dosage selection, and wherein the rotatable component may be coupled to a displacement mechanism for displacing the movable component with regard to the body. By rotating the rotatable component, the user can select a certain dosage to be injected. The rotation and dosage selection may be transferred by means of the displacement mechanism to a certain displacement of the movable component with regard to the body. Particularly, the higher dosage is selected, the more the displacement mechanism may move the movable component out of the body so that the air volume inside the body increases and the measurable capacitance changes accordingly.

The processor may be further configured to cause an indication to be output which informs a user of the end of the dwell time of the drug delivery device. The indication may be a visible and/or an audible signalling to the user or a signal transmitted to an external device such as a smartphone, which can itself signal to the user the end of the dwell time.

The processor may be configured to cause an indicator signal to be output at the start and/or the end of the dwell time of the drug delivery device. The indicator signal may be for example a visible and/or audible signal, such as activation of a LED or outputting a characteristic sound.

The drug delivery device may a powered auto-injector and wherein a dispensing mechanism of the powered auto-injector is powered by a pre-compressed spring.

The processor may be further configured to record information on an injection, particularly date and time of the injection.

A second aspect of this disclosure relates to a drug delivery device as disclosed herein and containing a medicament

DETAILED DESCRIPTION

Figure 1:
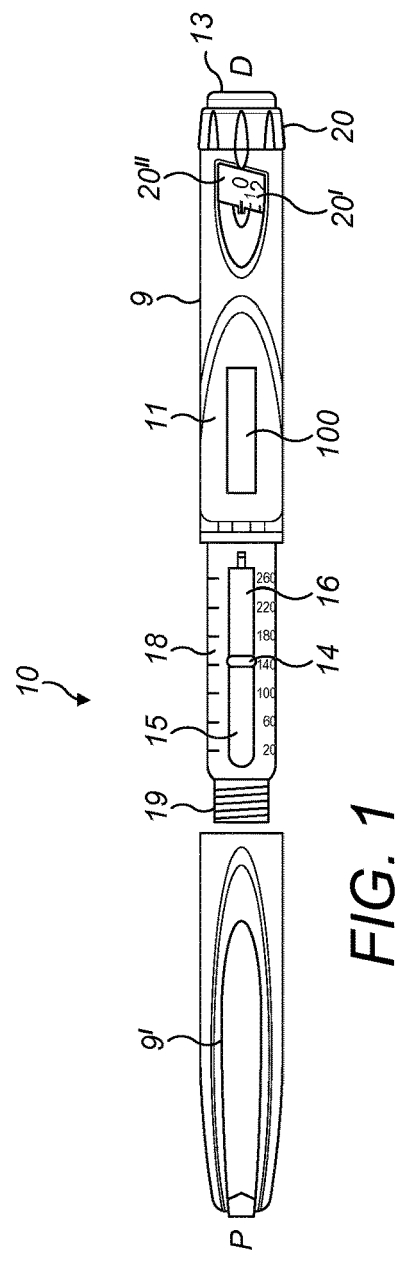
FIG. 1: a view of an injection device in form of a pen with dosage selection.
Figure 1:
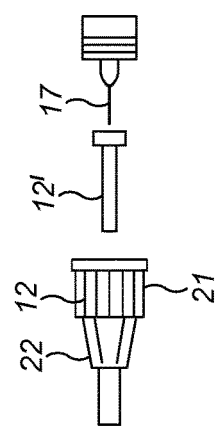

In the following, embodiments will be described with reference to an auto-injector. The present disclosure is however not limited to such application and may equally well be deployed with injection devices that eject other medicaments, or with other types of drug delivery devices, such as syringes, pre-filled syringes, needleless injectors and inhalers.

An injection device 10 according to embodiments will now be described with reference to FIG. 1. In some embodiments, the injection device 10 is a single use auto-injector 10. The auto-injector 10 has a proximal end P and a distal end D. The proximal end P is directed towards the injection site of a patient during an injection while the distal end D is directed away from the injection site.

The auto-injector 10 comprises a body 9 and a cap 12 (also referred to herein as the outer needle cap or ONC 12) and a further cap 12' (also referred to herein as the inner needle cap or INC 12'). The body 9 comprises an outer housing 11. The outer housing 11 is an elongate tube. The outer housing 11 includes a cartridge holder or syringe holder (not shown) which supports a cartridge or syringe 18 containing liquid medicament 16. Hereafter the description shall refer to a cartridge 18, which is supported by a cartridge holder (not shown).

The outer housing 11 also houses a dosage selection and injection or dispense mechanism (not shown) for causing dispensing of a selected dosage of the medicament 16 during injection. The dosage to be dispensed can be selected by means of a rotary knob 20 at the distal ned D of the auto-injector 10. The selection is shown on a mechanical scale 20' coupled with the rotary knob 20 through a window 20" in the outer housing 11.

A hollow needle 17 communicates with an interior volume of the cartridge 18 and serves as a conduit for liquid medicament 16 during injection. The needle 17 and the cartridge 18 are in a fixed position relative to each other and to the body 9. A stopper, plunger, piston or bung 14 is moveable within the cartridge 18 to as to expel medicament contained within the cartridge 18 through the needle 17 under action of the dispense mechanism.

The dispense mechanism is mechanically coupled to the piston 14 of cartridge 18. The dispense mechanism is configured to move the piston axially along the cartridge 18 in a proximal direction to dispense medicament 16 through the needle 17. The dispense mechanism includes components that cooperate to apply a force to the piston 14 in response to an actuation input provided by a user. Here, the actuation input that triggers application of a force to the piston 14 is received by way of a dose dispense button 13 that is located at the distal end of the auto-injector 10. The dispense mechanism is mechanically coupled to the dispense button 13.

The body 9 also comprises a cap support 19 at the proximal end of the outer housing 11. The cap support is concentric with the outer housing 11 and may have a smaller diameter. The cap support 19 extends from the proximal end of the housing 11. The ONC 12 is received over the cap support 19 to close the proximal end of the body 9 and to cover the needle 17. The ONC 12 comprises a cylindrical wall 21 and an end wall 22. With the ONC 12 located on the body 9, an internal surface of the cylindrical wall 21 abuts an external surface of the cap support 19 in tightly abutting relation so that the ONC 12 is retained thereon in an attached position.

To inject the medicament 16, the ONC 12 and INC 12' are removed from the device 10 by the user. Next, the dosage of the medicament 16 to be injected is selected by the user by turning the rotary knob 20 until the desired dosage is displayed on the mechanical scale 20'. The, the proximal end of the auto-injector 10 is placed against an injection site of a patient, which may be the user or another person. The user then actuates the dispense button 13. This causes the dispense mechanism to force the piston 14 to expel medicament from the cartridge 18 through the needle 17 into the injection site of the patient.

The cartridge 18 is transparent and a window 15 is provided in the housing 11 coincident with the cartridge 18 so that the medicament 16 contained within the cartridge 18 is visible. A user of the auto-injector this is able by inspection to determine whether the entire quantity of medicament 16 has been ejected from the cartridge 18 during the injection.

A label is provided on the housing 11. The label includes information 100 about the medicament included within the injection device 10, including information identifying the medicament. The information 100 identifying the medicament may be in the form of text. The information 100 identifying the medicament may also be in the form of a colour. The information 100 identifying the medicament may also be encoded into a barcode, QR code or the like. The information 100 identifying the medicament may also be in the form of a black and white pattern, a colour pattern or shading.

The proximal end P of auto-injector 10 can be protected with pen cap 9', which may be after usage of the auto-injector 10 mounted on the body 9 covering the proximal end P.

Figure 2:
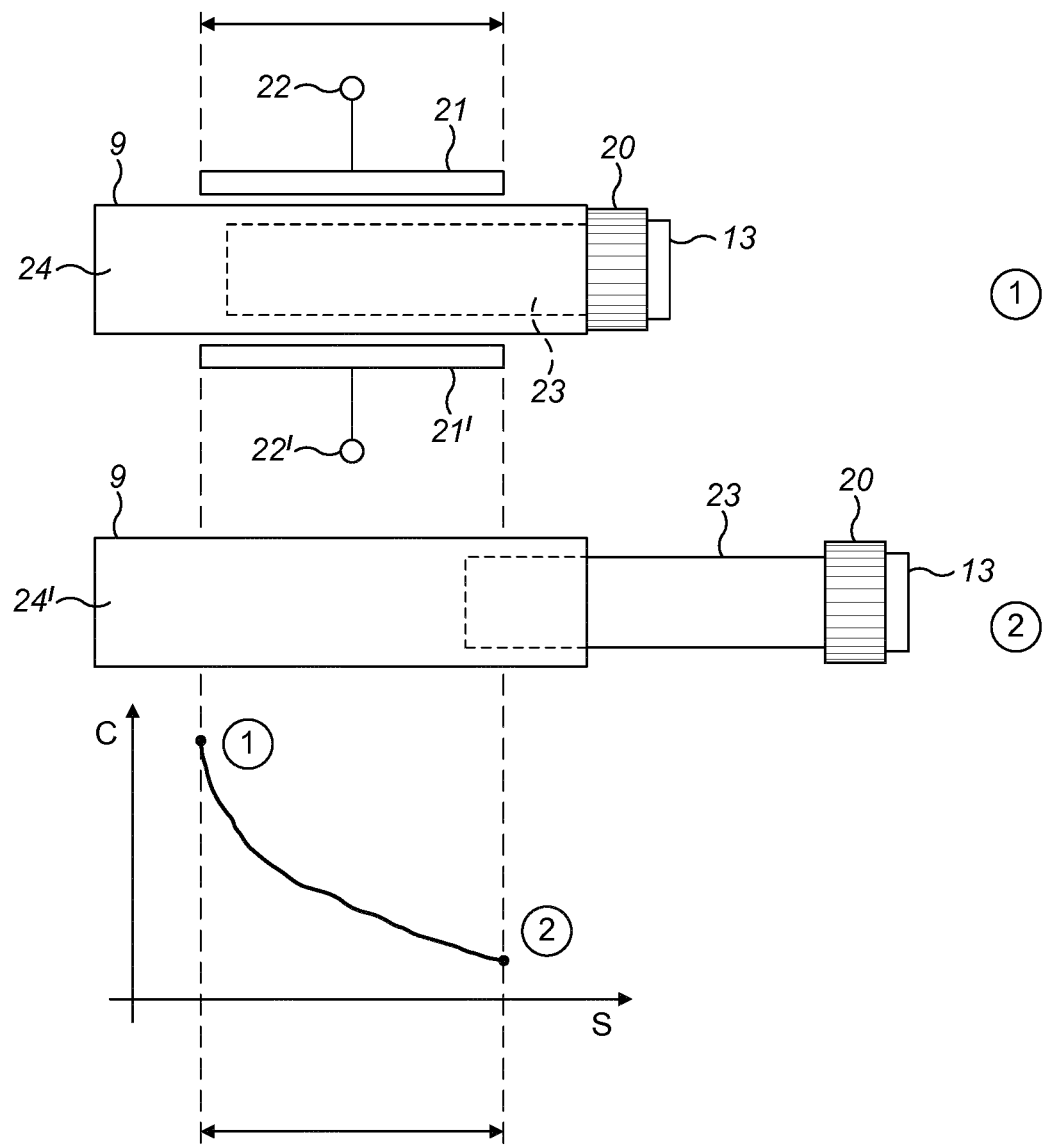
FIG. 2: a schematic illustration of an injection device and sensor components of the for capacitive sensing of the status of the injection device.

FIG. 2 shows a simplified schematic illustration of the injection device and sensor components of the for capacitive sensing of the status of the injection device.

From the injection device, the body 9 and a movable component 23 within the body are shown. The movable component 23 may comprise one or more parts of the dosage selection and injection or dispense mechanism, or may comprise the entire dosage selection and injection or dispense mechanism. The movable component 23 may also comprise at least metallic part, while all other parts as well as the body 9 are made of plastics, for example ABS (Acrylonitrile butadiene styrene) or POM (Polyoxymethylene). The metallic part may be for example a spring, or a sleeve. At the end of the movable component 23, the rotatory knob 20 for dosage selection and dispense button 13 are arranged.

By rotating the knob 20, a user may select the dosage to be dispensed. Rotation of the knob 20 results in a movement of the component 23 inside the body 9 along its longitudinal axis. Thus, the position of the component 23 in relation to the body 9 is changed. For example, a clockwise rotation of knob 20 may result in that the component 23 is moved outside the body 9, in FIG. 2 in the right direction as shown in the middle of FIG. 2, where the component 23 is moved wide out of the body 9. On the contrary, counter-clockwise rotation of the knob 20 may move the component 23 into the body 9 until the know 20 abuts on the edge of the body 9 and delimits a further move of the component 23 inside the body 9.

The outside of the body 9 comprises two metallic layers 21, 21' arranged opposite to each other. Both layers 21, 21' may cover only a part of the outside of the body 9, and each may comprise an electrical connector 22, 22' for connection with electronics of the injection device. The layers 21, 21' may extend along the longitudinal axis of the body 9 over a range, which comprises nearly the entire displacement of the movable component 23 inside the body 9, as shown in FIG. 2 by the double arrow at the top and the dashed vertical lines.

The displacement of the movable component 23 with regard to the body 9 by rotating the rotary knob 23 depending on the selected dosage alters the air volume from a smaller air volume 24 inside the body 9 to a larger air volume 24'. On the contrary, the air volume 24' is reduced to the air volume 24, when the movable component 23 is moved deeper inside the body 9 by selecting a respective dosage through rotating the rotary knob 20.

The alteration of the air volume 24, 24' and the displacement of the movable component 23 inside the body 9 influences the dielectric constant of the dielectric layer formed between the metallic layers 21, 21'. This again results in change of the capacitance of the capacitor formed by the metallic layers 21, 21' and the dielectric layer between them and formed by the air volume 24, 24', the body 9, and the movable component 23. The diagram at the bottom of FIG. 2 represents the change of the capacitance over the displacements of the movable component 23. At position (1), the capacitance is high since the movable component 23 is entirely moved into the body 9 and the air volume 24 is as small as possible. Thus, the dielectric constant is higher than at position (2), where the movable component 23 is entirely moved out of the body 9 and the air volume 24' is as large as possible. The capacitance decreases therefore from position (1) of the movable component 23 to position (2) of the movable component 23. This change of the capacitance is measurable and may be used for informing a user of the dwell time as will be explained below.

Figure 3:
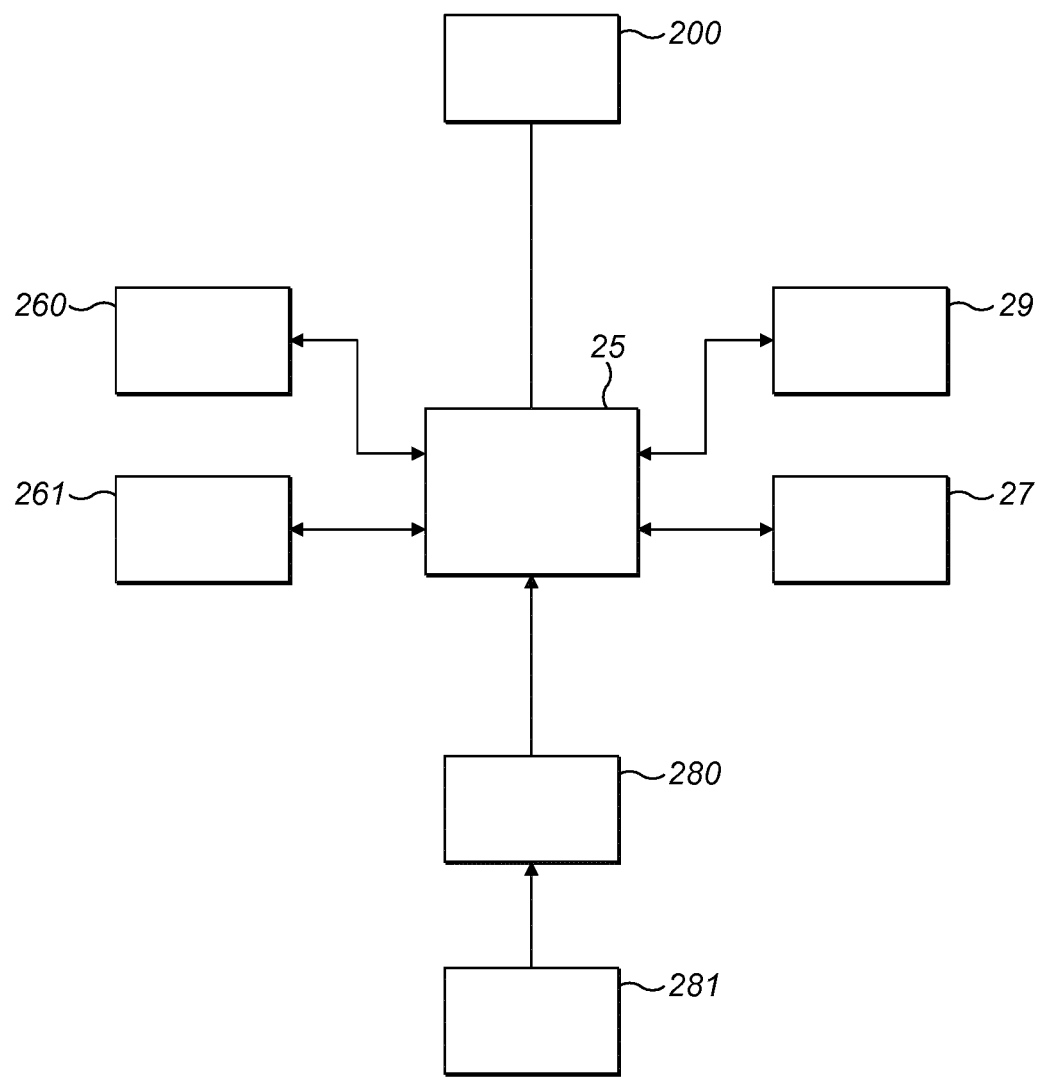
FIG. 3: a block diagram of electronic components of an injection device.

FIG. 3 shows a block diagram of electronic components of an injection device such as the injection device 10 of FIG. 1 equipped to measure the capacitance of the capacitor formed by the metallic layers 21, 21' and the components therebetween. The electronic components may comprise a processor 25, which may for instance be a microprocessor, a Digital Signal Processor (DSP), Application Specific Integrated Circuit (ASIC), Field Programmable Gate Array (FPGA) or the like. Processor 25 executes program code (e.g. software or firmware) stored in a program memory 260, and uses a main memory 261, for instance to store intermediate results. Main memory 261 may also be used to store a logbook on performed ejections/injections. Program memory 260 may for instance be a Read-Only Memory (ROM), and main memory may for instance be a Random-Access Memory (RAM).

The injection device may optionally further comprise at least one input transducer, for example a button (not shown in FIG. 3). This input transducer allows a user to turn on/off the electronics of the injection device, to trigger actions (for instance to cause establishment of a connection to or a pairing with another device, and/or to trigger transmission of information from injection device to another device), or to confirm something. In some other embodiments, the injection device may be automatically turned on/off via a sensor (not shown) detecting whether the ONC is put onto the injection device or not.

Processor 25 controls a display unit 29, which may be embodied as a Liquid Crystal Display (LCD) or an e ink display. Display unit 29 is used to display information to a user of injection device, for instance on present settings of injection device, or on a next injection to be given. Display unit 29 may also be embodied as a touch-screen display, for instance to receive user input.

Processor 25 also controls the capacitive sensor 200 (formed by formed by the metallic layers 21, 21' and the components therebetween and connected to the processor 25 via connections 22, 22'). The measurements received from the capacitive sensor 200 are indicative of the position of the movable component 23 within the body 9 of the injection device 10. The capacitive sensor 200 may collectively be referred to as non-contact sensor, since it is able to sense the absolute position and movement of components within the attached injection device 10 without contact between the sensor and any of the components sensed. The processor 25 receives these signals (voltage measurements) from the capacitive sensor 200 via connections 22, 22' and infers an operational state of the injection device 10 and causes information regarding the timing of the operation of the injection device 10 to be recorded in the main memory 261 and/or transmitted to an external device via a wireless unit 27. The operation of the sensor is described in greater detail with respect to FIG. 4.

Processor 24 controls the wireless unit 27, which is configured to transmit and/or receive information to/from another device in a wireless fashion. Such transmission may for instance be based on radio transmission or optical transmission. In some embodiments, the wireless unit 28 is a Bluetooth® transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form. The transmitted data may also include a time stamp associated with an injection.

Processor 25 may receive an input from an ONC sensor (not shown), which is operable to detect whether the outer needle cap 12 is present, i.e. to detect whether the outer needle cap 12 is coupled to the injection device 10. A battery 281 powers the processor 25 and other components by way of a power supply 280. The removal of the ONC 12 is detected by the ONC sensor and can be used as a wake-up or switch on trigger. Thus, the injection device may automatically turn on and begin its monitoring processes when the ONC 12 is removed. Similarly, when the ONC 12 is replaced the injection device may automatically power off, thus saving battery power.

The electronics of FIG. 3 is thus capable of determining information related to a condition and/or use of injection device 10. This information may be displayed on the display 29 for use by the user of the device. The information may be either processed by injection device 10 itself, or may at least partially be provided to another device (e.g. a blood glucose monitoring system or a computing device).

The processor 25 may be configured to receive signals form the ONC sensor and to detect when the ONC 12 is not attached to the injection device 10. If the user stores the injection device 10 without the ONC 12 attached, then the needle 17 can become clogged. Therefore, the injection device 10 may be configured to produce an indicator signal if the processor 25 detects that the ONC 12 has been un-attached for a predetermined length of time following an injection operation. The indicator signal may be sent via the wireless unit 27 to the external user device such that the user can be alerted to the need to replace the ONC 12 even if they have moved away from the injection device 10. Alternatively, or in addition, the indicator signal may comprise the injection device 10 displaying words and/or graphics on the display unit 29 or producing sound.

The injection device 10 comprises a capacitive sensor formed by the metallic layers 21, 21' and the components therebetween. Referring now to FIG. 4, the operation of the capacitive sensor will be described in greater detail.

Figure 4A:
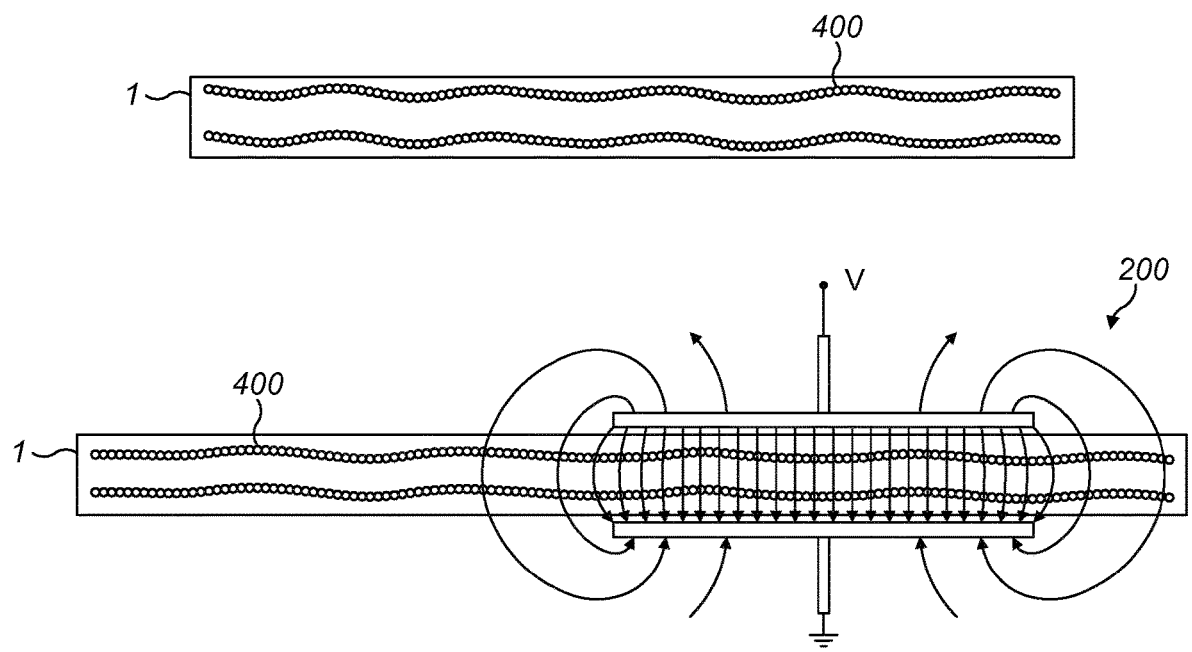
FIG. 4a: a schematic illustration of an injection device and sensor components of the supplementary device for capacitive sensing of the status of the injection device.

FIG. 4a illustrates shows diagrammatically a cut-away through the injection device 10 when the injection device is in a pre-injection configuration and a post injection configuration (also referred to as pre-activation and post-activation). The injection device 10 comprises a drive spring 400, which is pre-compressed during assembly of the injection device 1. The drive spring 400 is maintained in this pre-compressed state until an injection is performed. When a user triggers an injection operation by pressing dose dispense button 13, the dispense mechanism is released and the drive spring decompresses so as to dispense medicament from the cartridge 18.

Various components of the capacitive sensor 200 are shown schematically in the lower image in FIG. 4a. The capacitive sensor 200 comprises opposing sets of at least one electrically conductive plate (in FIG. 2 the metallic layers 21, 21'). The plates are connected in a circuit so as to form a capacitor. The injection device 10 occupies the space between the plates and functions as the dielectric layer of the capacitor. The capacitive sensor 200 sends signals to the processor 25 via which the processor 25 can determine the effective capacitance. For example, the processor 25 may control the application of charge to one plate of the capacitive sensor 200 and then measure the time taken for the capacitive sensor 200 to discharge.

The upper image in FIG. 4a shows the approximate position of the drive spring 400 before an injection has been performed. The drive spring 400 is compressed, with the coils of the spring being closely spaced or touching. The lower image in FIG. 4a shows the approximate position of the drive spring 400 after the energy stored therein has been released during an injection process. The coils of the drive spring are spaced further apart. In some embodiments, the drive spring is metallic.

Figure 4B:
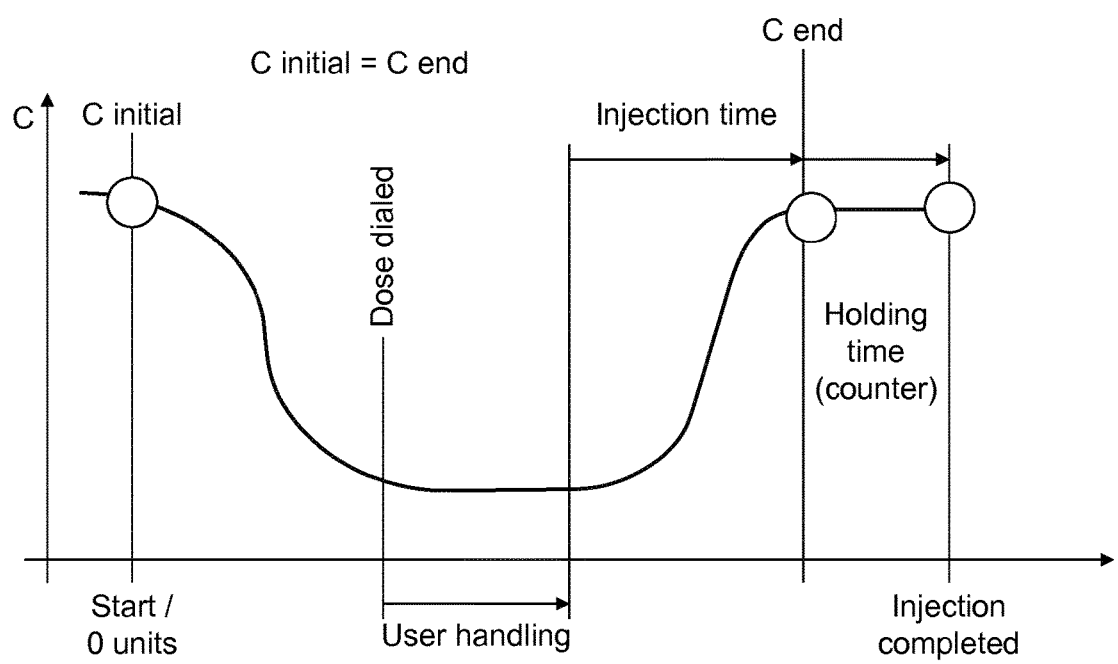
FIG. 4b: a graph illustrating the measured capacitance depending on the position of the movable component within the body during an injection procedure of the injection device.

FIG. 4b is a graph showing an exemplary relationship between capacitance and charge before, during and after an injection process. Before the injection device 1 is used, the capacitance measured by the capacitive sensor 200 is relatively high, due to the presence of a greater amount of the drive spring 400 in the region between the capacitor plates and the non-selection of a dosage, which results in the movable component 23 entirely positioned within the body 9 of the injection device 10. Then, a user selects a dosage to be injected by rotating the rotation knob 20 and displacing the movable component 23 such that it is moved out of the body 9 of the injection device 10, which results in a decrease of the capacitance measured by the capacitive sensor 200 until the dosage is set (at point "set dose" in FIG. 4b). The drive spring 400 is part of the movable component 23 and moved out of the body 9. The start and end points of the medicament ejection process are shown by the injection time arrow. The injection and medicament ejection are started when the user presses the dispense button 13. This incurs that the movable component 23 is moved again into the body 9 while the drive spring 400 uncoils. Thus, the materials of the movable component 23 is disposed in the region between the capacitor plates of the capacitance sensor 200 until the movable component 23 reaches its start position, i.e. when no dosage is selected. Therefore, the capacitance measured by the capacitive sensor 200 increases during the ejection. After the injection device 10 has been used, the capacitance measured by the capacitive sensor 200 has reached its start value again.

The processor 25 may be configured to determine that an injection has been completed if the measured capacitance reaches the second time its start value (designated as "injection completed" in FIG. 4b). The processor 25 is configured to compare the capacitance measurements on a continuous basis during the injection with the capacitance measured at the beginning of usage of the injection device 10 and before a dosage was selected. This measured capacitance is stored in the main memory 261 as initial capacitance. After storing the measured capacitance, the processor 25 may set a flag indicating that it is ready for capacitance measurements during the injection. The processor 25 then continuously receives and processes measurements from the capacitive sensor 200. When the processor 25 detects that the user has pressed the dispenser button 13, for example by detecting a sudden increase of the measured capacitance, it may compare each received capacitance measurement with the stored initial capacitance. When the processor 25 detects that the received measurements of the capacitance correlate with the stored initial capacitance, it starts an internal timer set to a predefined holding time. The processor 25 may at the same time cause an indication to be output for informing the user of the end of the injection and the begin of a dwell time. The indication may be a signal to configure the display unit 29 to display information on the end of injection and begin of dwell time. Also, a sound may be generated via some sound equipment. When the timer reaches the dwell time, the processor 25 may cause a further indication to be output for informing the user of the end of dwell time. The indication may be a signal to configure the display unit 29 to display information on the end of dwell time. Also, again, a sound may be generated via some sound equipment.

The capacitive sensor 200 may be shielded to protect it from external electromagnetic impulses.

The processor 25 may be configured to record a user's injection history. The processor 25 may have an internal clock to create time stamps associated with the injection events. The clock may be a relative clock or an absolute clock. The injection device 10 may be configured to communicate with an external device through wireless unit 27 and the external device may provide an absolute time.

When a user performs an injection, this may be detected by the capacitive sensor 200 as described above. A time stamp associated with the injection may then be created by the processor 25. The processor 25 may also record and associate with the time stamp the type of medicament injected, using for example previously read information. An external device (not shown) in the user's possession may be registered and associated with the injection device 10. The external device may be a mobile computer or smart phone via the wireless unit 27. The mobile computer or smart phone may run a computer program for managing the user's medical records and injection history. The injection device 10 may be configured to communicate the recorded injection information to the external device.

The processor 25 may be pre-programmed with information relating to the frequency at which the user should perform injections. This programming may take the form of a maximum time between injections or a medical regimen associated with the user of the injection device 10. For example, the processor 25 may be pre-programmed with information specifying that the maximum time between injections should be 24 hours. In some other embodiments, the medical regimen may be more detailed, such as to specify specific times of day at which the user is to perform an injection operation using the injection device 10. Alternatively, the processor 25 may be configured to calculate a time at which the user should next perform an injection based on the injection history. For example, the time at which the user should perform the next injection may depend on the amount of medicament previously injected and the frequency of the previous injections. The processor may use the previous injection history to calculate a medical regimen for the user.

When the processor 25 determines that it is time for the user to perform a subsequent injection, it causes a reminder signal to be sent via the wireless unit 27 to the associated external device. The external device may then notify and remind the user that their next injection is due. This is advantageous as the user may not wish to carry the injection device 10 with them, but may in any case by carrying a smart phone or similar device. Thus, the user can be reminded of the need for a subsequent injection via a separate device which they carry with them. Furthermore, the injection device 10 may need to be kept under specific conditions, such as in a refrigerator or a freezer, such that it is not possible for a user to carry the injection device with them. It is therefore easy for a user to forget about the times at which an injection needs to be performed.

Examples above relating to insulin, for diabetic users, are illustrative. The present disclosure is also applicable to any users who may become impaired. For instance, patients who require cardiovascular medication or patients who require painkillers, such as a COX-2 inhibitor.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A drug delivery device comprising:
   a body;
   a movable component arranged inside the body;
   a dosage selection and injection mechanism setting a position of the movable component inside the body depending on a selected dosage;
   a non-contact sensor configured to output signals indicative of the position of the movable component inside the body; and
   a processor configured to receive the signals output from the non-contact sensor and to determine based on the signals whether the movable component is either in an initial position inside the body corresponding to no selected dosage or is in a selected dosage position, wherein upon determining that the movable component has changed its position from the selected dosage position to the initial position, the processor is configured to cause an indication to be output to inform a user regarding a dwell time of the drug delivery device;
   wherein the non-contact sensor is a capacitive sensor, and wherein the body, the movable component and the dosage selection and injection mechanism form at least a part of a dielectric layer of the capacitive sensor; and
   wherein the processor is further configured to measure a capacitance of the capacitive sensor when no dosage is selected and the movable component is in the initial position inside the body, to store the measured capacitance as a reference value, to detect a capacitance change when a dosage is selected, to detect a further capacitance change due to an injection and to determine an end of the injection when the measured capacitance correlates with the reference value.

2. The drug delivery device according to claim 1, further comprising a display unit,
   wherein causing the indication to be output comprises causing one or more graphical elements to be displayed on the display unit, the one or more graphical elements communicating a progress of the dwell time.

3. The drug delivery device according to claim 1, further comprising a transmission unit,
   wherein causing the indication to be output comprises causing one or more signals to be transmitted by the transmission unit, the one or more signals communicating a progress of the dwell time.

4. The drug delivery device according to claim 3, wherein the transmission unit is a wireless unit for transmitting data to one or more external devices.

5. The drug delivery device according to claim 1, wherein the body, the movable component and parts of the dosage selection and injection mechanism are made of one or more materials selected to obtain a dielectric constant of the capacitive sensor sufficient to determine whether the movable component is either in the initial position inside the body corresponding to no selected dosage or in the selected dosage position, wherein the one or more materials comprise at least one of plastics or metal.

6. The drug delivery device according to claim 5, wherein at least one movable part of the dosage selection and injection mechanism is made of metal, which influences a dielectric property of the capacitive sensor.

7. The drug delivery device according to claim 6, wherein the at least one movable part of the dosage selection and injection mechanism is a drive spring of the drug delivery device.

8. The drug delivery device according to claim 1, wherein the capacitive sensor comprises opposing sets of at least two electrically conductive parts with a first part being a layer arranged on at least a part of an outside of the body.

9. The drug delivery device according to claim 8, wherein a second part of the at least two electrically conductive parts is a layer arranged on at least a part of the outside of the body and opposite to the first part.

10. The drug delivery device according to claim 8, wherein a second part of the at least two electrically conductive parts is arranged inside the body and opposite to the first part, wherein each of the body, the movable component and the dosage selection and injection mechanism is at least partly arranged between the first and the second part.

11. The drug delivery device according to claim 1, wherein the dosage selection and injection mechanism comprises a display for the selected dosage, wherein the display is coupled to a dosage selection rotatable component, and wherein the dosage selection rotatable component is coupled to a displacement mechanism configured to displace the movable component with regard to the body.

12. The drug delivery device of claim 1, wherein the processor is further configured to cause another indication to be output to inform the user of an end of the dwell time of the drug delivery device.

13. The drug delivery device according to claim 1, wherein the processor is configured to cause an indicator signal to be output at a start, an end, or both at the start and the end of the dwell time of the drug delivery device.

14. The drug delivery device according to claim 1, wherein the drug delivery device is a powered auto-injector, and wherein a dispensing mechanism of the powered auto-injector is powered by a pre-compressed spring.

15. The drug delivery device according to claim 1, wherein the processor is further configured to record information of the injection, the information including date and time of the injection.

16. The drug delivery device according to claim 1, wherein the drug delivery device contains a medicament.

17. A method of determining a dwell time of a drug delivery device, the method comprising:
   generating, by a non-contact sensor, signals indicative of a position of a movable component inside a body of the drug delivery device, wherein the non-contact sensor is a capacitive sensor, wherein the body, the movable component and a dosage selection and injection mechanism form at least a part of a dielectric layer of the capacitive sensor;
   receiving, by a processor, the signals to determine based on the signals whether the movable component is either in an initial position inside the body corresponding to no selected dosage or is in a selected dosage position; and
   determining, by the processor, that the movable component has changed from the selected dosage position to the initial position, and in response:
      causing, by the processor, an indication to be output to inform a user regarding the dwell time of the drug delivery device.

18. The method of claim 17, further comprising:
measuring, by the processor, a capacitance of the capacitive sensor when no dosage is selected and the movable component is in the initial position inside the body; and
storing the measured capacitance as a reference value, to detect a capacitance change when a dosage is selected, to detect a further capacitance change due to an injection and to determine an end of the injection when the measured capacitance correlates with the reference value.

19. The method of claim 18, wherein the capacitive sensor comprises opposing sets of at least two electrically conductive parts with a first part being a layer arranged on at least a part of an outside of the body and a second part being a layer arranged on at least a part of the outside of the body and opposite to the first part.

20. The method of claim 18, wherein the capacitive sensor comprises opposing sets of at least two electrically conductive parts with a first part being a layer arranged on at least a part of an outside of the body and a second part being arranged inside the body and opposite to the first part,
wherein each of the body, the movable component and the dosage selection and injection mechanism is at least partly arranged between the first and the second part.

\* \* \* \* \*